United States Patent [19]

Levin

[11] Patent Number: 5,209,931
[45] Date of Patent: May 11, 1993

[54] STABILIZED PVC PRODUCTS AND THEIR PRODUCTION

[75] Inventor: Gideon Levin, Rehovot, Israel

[73] Assignee: Yeda Research and Development Co. Ltd., Rehovot, Israel

[21] Appl. No.: 762,118

[22] Filed: Sep. 19, 1991

[30] Foreign Application Priority Data

Sep. 19, 1990 [IL] Israel .......................................... 95732

[51] Int. Cl.$^5$ ........................ A01N 25/00; A61K 9/14; C08J 3/24
[52] U.S. Cl. ..................................... 424/405; 424/487; 523/122
[58] Field of Search .......................... 525/331.5, 331.6; 523/122; 424/405, 487

[56] References Cited

U.S. PATENT DOCUMENTS

| | | | |
|---|---|---|---|
| 2,438,097 | 3/1948 | Rogers et al. | 260/86 |
| 2,466,998 | 4/1949 | Rogers et al. | 260/86 |
| 3,808,173 | 4/1974 | Orihashi | 260/47 R |
| 4,405,360 | 9/1983 | Cardarelli | 71/117 |
| 4,806,393 | 2/1989 | Levin | 427/384 |

FOREIGN PATENT DOCUMENTS 1203442 8/1970 United Kingdom .

OTHER PUBLICATIONS

Mori, Kunio et al. Modification of Poly(vinyl chloride), J. Polymer Science: Part A-1, #3, vol. 9, 639-650 (1971).

Primary Examiner—Thurman K. Page
Assistant Examiner—N. Levy
Attorney, Agent, or Firm—Browdy and Neimark

[57] ABSTRACT

Crosslinked plasticized or unplasticized PVC products having gradient crosslinking density, with a high crosslinking density on the outer surface and a low or none crosslinking density at the bulk of the product, are prepared by immersing the PVC product in a hot water solution of a crosslinking material and a phase transfer catalyst. The products obtained provide controlled release of substances occluded within the PVC matrix, thus preventing leakage of plasticizers, stabilizers and other additives, and permitting controlled slow release of substances like pesticides, fertilizers, drugs and the like, into the surrounding environment.

24 Claims, 1 Drawing Sheet

THE EFFECT OF TYPE TREATMENT OF PLASTICIZED PVC TUBE ON THE AMOUNT OF PLASTICIZER EXTRACTION

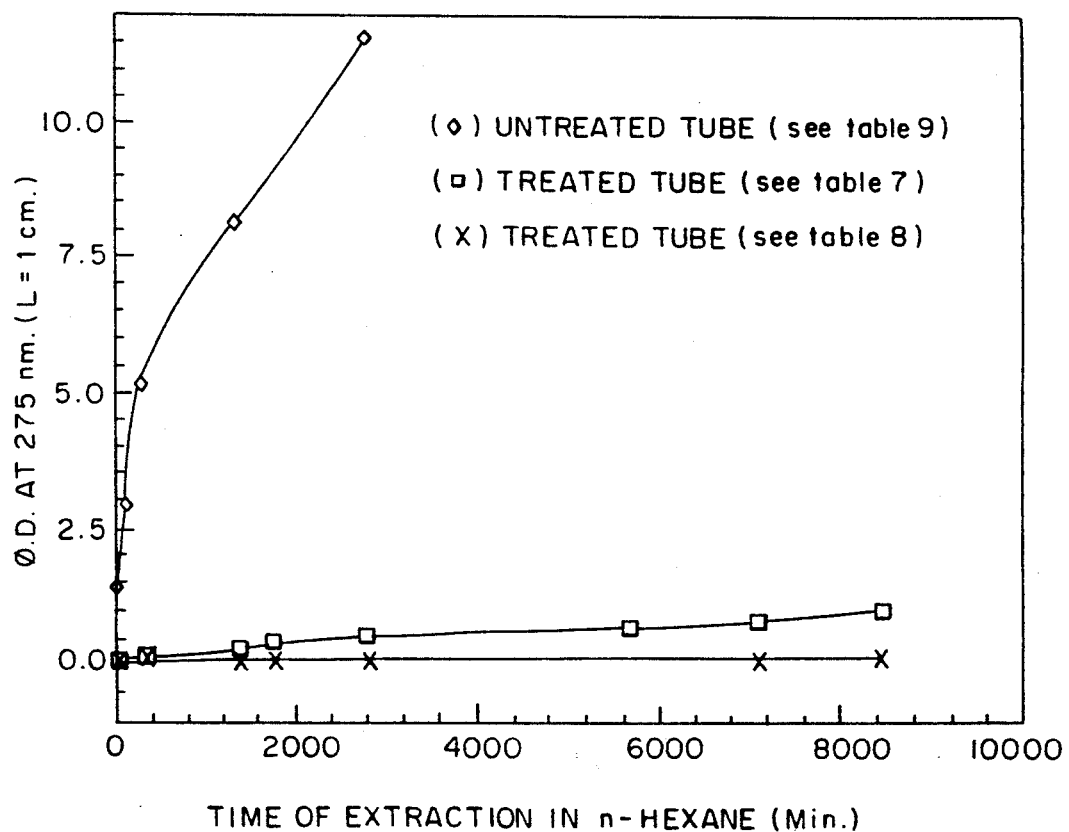

STABILIZED PVC PRODUCTS AND THEIR PRODUCTION

FIELD OF THE INVENTION

The present invention relates to a process for the preparation of crosslinked PVC products, and more particularly to crosslinked plasticized or unplasticized PVC products wherefrom the release of an occluded substance can be controlled, thus either preventing the leakage of plasticizers, stabilizers and other additives, and/or providing controlled release of pesticides, fertilizers, drugs and other materials.

BACKGROUND OF THE INVENTION

Polyvinyl chloride (PVC) is the best known and most widely used of the vinyl plastics, accounting for about 30% of the plastics used worldwide. For many uses, the PVC has to be used in plasticized form. The plasticizer, usually a high-boiling liquid, is added by mixing with the PVC and preserves its flexibility. However, with time the plasticizer gradually escapes from the PVC object, rendering it brittle and breakable.

Various attempts have been made in the past to produce crosslinked PVC in order to prevent plasticizer migration. Amongst these there may be mentioned UV irradiation of a mixture of trimethylpropane trimethylacrylate with PVC, resulting in a crosslinked polymer which has thermal stability and improved abrasion resistance. Also compounds such as trialkylacrylates, triallylisocyanurate, allyl esters, divinylbenzene and triacrylates have been used as crosslinking agents. When such materials are added to the entire polymer, the crosslinking results in a brittle polymer which is difficult, if not impossible, to mold, and/or a product which is undesirably brittle.

Attempts have also been made to use a protective layer of epoxyacrylate as a surface layer to a PVC substrate, the epoxyacrylate being crosslinked by application of UV radiation. These attempts resulted in a layer having poor adhesion to the PVC substrate. A further attempt in this direction was disclosed recently in the patent U.S. No. 4,806,393, issued to the same applicant, which describes the coating of a plasticized PVC substrate with a thin layer of a cross-linkable thiocarbamate modified PVC and crosslinking by heating. Although this layer may prevent the leakage of plasticizers, the process has the disadvantages of requiring a special oven for the removal of the solvent used when applying the modified PVC on the substrate and for the crosslinking step. Other disadvantages of this process include the need of the preparation of the starting product in a preliminary step by reaction of PVC and the thiocarbamate, resulting in an unstable crosslinkable product which, on storage, may crosslink by itself. Besides, it is very difficult to control the temperature of the reaction. Above 45° C., the material may crosslink by itself and will not dissolve in the solvent, thus making impossible its use for coating a PVC substrate.

Thin films, tubes or beads of size $\geq 0.1$ $\mu$ made of PVC, plasticized PVC or copolymers of PVC are used as a means for controlled release of pesticides, fertilizers and even drugs into the surrounding environment. However, there are difficulties in this technique because in many cases the release is too fast, in which cases the beads have to be replaced very often and become less efficient.

These and other disadvantages of the prior art are overcome by the process of the invention.

SUMMARY OF THE INVENTION

It is an object of the present invention to overcome the deficiencies in the prior art, such as mentioned above, and to provide an improved process in which there is no need to synthesize and purify the reagents used to modify the PVC or to use a solvent to form the crosslinked layer on the PVC, as in the process of U.S. No. 4,806,393.

According to the present invention, a process is provided for the preparation of crosslinked plasticized and unplasticized PVC products in which the PVC product is immersed in a hot water solution containing a crosslinking material and a phase transfer catalyst. The reagents diffuse into the PVC material; displace one or more chlorine atoms along the polymeric chain and trigger a chemical crosslinking of the substituted polymer molecules, thus forming a product with a modified surface consisting of a tight polymer network.

According to this process a crosslinked PVC product is obtained, characterized by a gradient crosslinking density, having a high crosslinking density on the outer surface and /or near the surface and a low or no crosslinking density within the bulk of the product. The formation of this crosslinked structure inside the material, with a higher density near the surface, allows controlled release of substances occluded within the material, thus preventing migration of plasticizers, stabilizers and other additives, to the boundary, and their discharge into the surroundings, and/or enabling controlled slow release of substances, like pesticides, fertilizers or drugs.

The invention also relates to a crosslinked plasticized or unplasticized PVC product characterized by a gradient crosslinking density that is high on the outer surface and/or near the surface of the product and low or none at its bulk.

The invention further relates to a process for controlled release of substances occluded within a PVC product which comprises immersion of the PVC product in a hot water solution of a crosslinking agent and a phase transfer catalyst.

BRIEF DESCRIPTION OF THE DRAWING

FIG. 1. Shows the effect of treatment type on plasticizer extraction.

DETAILED DESCRIPTION OF THE INVENTION

The PVC product according to the invention may be made of PVC alone or of a copolymer of PVC, e.g., PVC-polyvinyl acetate, PVC-polyvinyl alcohol, PVC-polyacrylonitrile and the like. It may be plasticized or unplasticized.

In the process of the present invention, a crosslinking material is dissolved in hot water in the presence of a phase transfer catalyst, and a PVC product in the form of film, tube, beads or any other shape, is immersed in the solution. The crosslinking material, with the aid of the phase transfer catalyst, is diffused from the water to the solid polymeric material, thus reacting with the polymer in a typical nucleophilic reaction, followed by a crosslinking reaction, and resulting in a PVC product with a high crosslinking density on the outer surface diminishing towards the bulk of the product. Post treatment of the crosslinked surface of the PVC product with a water solution of an inorganic or organic salt results in further changes that either enhance protection against plasticizer migration or permit controlled slow release of substances from the polymer matrix outside.

The preferred crosslinking materials are polyfunctional thiol compounds and dithiocarbamate derivatives. The polyfunctional thiol compound may be a dithiol or a trithiol derivative of the general formulas

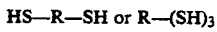

HS—R—SH or R—(SH)$_3$ wherein R is an alkyl, aryl, aralkyl or heterocyclic radical or a radical derived from a polyalkylene oxide, such as polyethylene oxide or polypropylene oxide. Examples of aryl radicals are phenyl and naphthyl, and of heterocyclic radicals are pyridyl and triazinyl.

In a preferred embodiment, the crosslinking material is an N,N-disubstituted dithiocarbamate, preferably of the formula

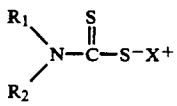

wherein $R_1$ is alkyl, optionally substituted by hydroxy or acyloxy, or $R_1$ is aralkyl; $R_2$ is hydrogen or $R_1$, or $R_1$ and $R_2$ together with the N atom form a ring optionally containing an N, S or O atom and/or a carbonyl group and being optionally condensed to a benzene ring, and $X^+$ is a cation Preferred alkyl radicals are lower alkyls, e.g. ethyl, and a preferred aralkyl radical is benzyl.

Preferred acyloxy groups are radicals derived from aliphatic and aromatic carboxylic acids, e.g., acetic acid, propionic acid, benzoic acid, phthalic acid and the like, but also moieties derived from organic phosphoric and phosphonic acids are encompassed by the invention. If desired, the acyloxy group is a moiety compatible with the plasticizer molecule of the plasticized PVC product.

Examples of rings formed by $R_1$ and $R_2$ together with the N atom are morpholine, piperidine or a ring of the formula

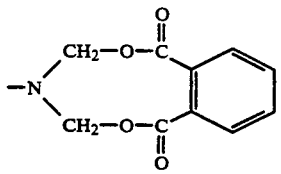

The dithiocarbamate compound may also be prepared in situ by the reaction of carbon disulfide with a suitable primary or secondary amine under basic conditions, such as in a sodium hydroxide solution, according to the following reaction.

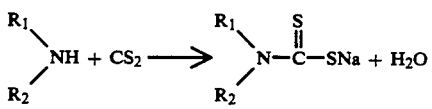

Suitable phase transfer catalysts include quaternary ammonium salts, tertiary alkyl phosphonium salts, poly-ethers such as $C_6$–$C_{15}$ polyethylene oxide, and cyclic ethers, such as crown ethers.

Preferred phase transfer catalysts are quaternary ammonium salts of the formula

$$R_3 R_4 R_5 R_6 N^+ Y^-$$

wherein $R_3$–$R_6$ are the same or different alkyl radicals and $Y^-$ is an anion, such as $ClO_4^-$, $ClO_3^{31}$, $NO_3^-$, $PO_4^{3-}$, $CO_3^{2-}$, Halogen$^-$ and $HSO_4^-$. Preferably, $R_3$–$R_6$ are butyl and $Y^-$ is an halogen ion or hydrogen sulfate.

In the process of the invention, the PVC product in the form of a film or any other structure is dipped in a hot water solution which contains the phase transfer catalyst and the crosslinking material or the reactants for its preparation in situ.

The temperature of the water, the concentration of the reagents, the time of immersion and the post treatment of the product are responsible for the degree of crosslinking of the polymeric material, and thus establish the rate at which the material occluded within the PVC matrix is released.

The temperature of the water solution according to the invention may be in the range of from about 60°–90° C. At these temperatures, the crosslinker diffuses through the PVC, displaces one or more chlorine atoms along the polymeric chain and the PVC is subsequently crosslinked. The concentration of the phase transfer catalyst may be in the range between 0.1% and 5% and of the crosslinker in the range of 2% and 10%, both based on the water, but it should be understood that other quantities may also be used. The time of immersion of the PVC product in the hot water solution will vary according to the water temperature, and usually will decrease with increase of the temperature.

After the treatment with the crosslinking material and the phase transfer catalyst, the crosslinked PVC product may be further immersed in a water solution of an organic or inorganic salt, containing a cation such as an alkali, earth alkaline or transition metal residue and an anion such as $NO_3^-$, $SO_4^{2-}$, $PO_4^{3-}$ or $CF_3COO^-$. In an alternative approach, the organic or inorganic salt is added directly to the water solution containing the crosslinking material and the phase transfer catalyst. The organic or inorganic salt addition will result in replacement of chlorine ions by the anions of the salt, improving the properties of the product.

The crosslinked PVC products of the invention have different degrees of substitution. For example the products may have an average of 1 out of every 2-3 chlorine atoms substituted by the crosslinking material near the surface and 1 out of 10 chlorine atoms or even more substituted at a further distance from the surface.

The invention will now be illustrated by the following non-limiting examples:

EXAMPLE 1

A film of plasticized PVC was prepared by casting a 10% tetrahydrofuran (THF) solution of polyvinyl chloride (PVC) and the plasticizer dioctylphthalate (DOP) in a weight ratio of 70:30 on a glass plate, and working out with a doctor's blade. The final thickness of the dry film was about 60–70μ. After immersion for 80 min at 65° C. in a water solution comprising 600 ml water, 30 or sodium diethyldithiocarbamate and 15 g tetrabutylammonium chloride, the plasticized PVC film was removed, washed with water and dried under vacuum for 20 hr. It was then further washed with water for 19 hr, and extracted with hexane for 34 hr at room temperature. The properties of the so treated plasticized PVC film were compared to those of an untreated plasticized PVC film after hexane extraction. The results are summarized in Table 1.

TABLE 1

| PROPERTY | TREATED SAMPLE | UNTREATED SAMPLE |
|---|---|---|
| solubility in THF | Gel not soluble | completely soluble |
| % sulfur | 4.75 | 0.0 |
| change in weight after 36 hr of extraction | (+)4.53 | (−)13.1 |
| physical appearance | flexible | brittle |

EXAMPLE 2

Plasticized PVC films (20μ) with 50% of platicizer (DOP) were immersed in 300 ml water solution containing 11.2 g sodium diethyldithiocarbamate and 5.6 g tetrabutylammonium chloride at 88° C. for different periods of time. The properties of grafted and untreated films as function of contact time are summarized in Table 2.

TABLE 2

| SAMPLE # | TIME OF CONTACT (min.) | SOLUBILITY IN T.H.F | % OF WEIGHT LOSS OR GAIN AFTER 24 hr. EXTRACTION IN HEXANE | % Cl | % S |
|---|---|---|---|---|---|
| 0 | 0 | S | −21.9 | | |
| 1 | 1 | S | −9.6 | 40.38 | 3.83 |
| 3 | 3 | S | +1.0 | 36.30 | 7.06 |
| 7 | 7 | S | +14.1 | 30.92 | 9.9 |
| 13 | 13 | N.S | +40.7 | 22.63 | 15.73 |
| 15 | 15 | N.S | +42.3 | — | — |

S soluble
N.S. partially or not soluble
The % of weight gain is due to solvent penetration into the film.

EXAMPLE 3

Films of the following composition were cast on a glass plate: PVC: 50 g, DOP: 16 gr and THF:: 630 gr. The films were dried overnight at room temperature and then put in a vacuum oven at 60° C. for 24 hr. The percent of chlorine was 42.22%.

The films were immersed at 60° C. for 2 hours in a solution of the following composition: sodium diethyldithiocarbamate (5.0 g), phase transfer catalyst (2.5 gr) and water (50.0 g). The effects of different phase transfer catalysts in the plasticizer migration, are shown in Table 3.

TABLE 3

| EXAMPLE | PHASE TRANSFER | SOLUBILITY IN THF | % S | % Cl |
|---|---|---|---|---|
| 393 | tetrabutyl ammonium fluoride | not soluble | 13.75 | 23.76 |
| 394 | tetrabutyl ammonium chloride | not soluble | 13.89 | 20.81 |
| 396 | tetrabutyl ammonium iodide | soluble | 9.90 | 22.10 |

The films were subjected to vacuum at room temperature for 12 hr and then at 50° for 3 hr, further treated with water for 17 hrs and vacuum dried for 24 hr. Extraction in hexane was carried for as long as 379 hr. The weight loss or gain and physical properties after hexane extraction are given in Table 4.

TABLE 4

| SAMPLE | % weight change after hexane extraction | | | | | | | |
|---|---|---|---|---|---|---|---|---|
| | 2 hr | 4 hr | 10 hr | 34 hr | 130 hr | 252 hr | AFTER VACUUM | 399 hr |
| 393 | 3.7 | 5.2 | 5.6 | 7.2 | 9.8 | 10.3 | 1.52 | 3.65 |
| 394 | 5.06 | 8.40 | 6.20 | 7.5 | 12.3 | 6.3 | 3.08 | 5.45 |
| 396 | 6.3 | 8.8 | 8.8 | 4.8 | 17.4 | 12.8 | −0.05 | 4.48 |

EXAMPLE 4

Extraction comparison of reacted and unreacted plasticized tubes

A plasticized PVC tube (37.4% DOP) with internal diameter of 6 mm and wall thickness of 1mm, was immersed for 2¼hr at 89° C. in a water solution containing 12.5 g sodium diethyldithiocarbamate and 3.75 g tetrabutylammonium hydrogensulfate in 250 ml water. The tube was then washed in water, dried and then immersed in 150 ml n-hexane. The n-hexane solution was analyzed for its DOP content as a function of extraction time. At the same time, the gain or lost weight of the tube was checked. At the end of the experiments, the treated tube was dissolved in tetrahydrofuran. As a result of the treatment, some crosslinking of the PVC chains occurred, leading to undissovled material. The sulfur and the chlorine contents of the undissolved PVC were determined. The soluble material in the tetrahydrofuran solution was added to methanol to precipitate the solubel PVC. The amount of DOP that remained in the tetrahydrofuran/methanol solution was measured using optical spectroscopy.

An untreated tue with similar characters of the treated plasticized PVC tube was also immersed in 150 ml n-hexane. The concentration of DOP in the n-hexane and the weight change as function of the extraction time for both the treated and untreated samples, are shown in the following Tables 5 and 6, respectively.

TABLE 5

TREATED TUBE (initial weight of tube was 1.296 g.)

| EXTRACTION TIME IN HEXANE (MIN.) | % WEIGHT LOST (−) GAIN (+) | CONCENTRATION OF DOP IN THE HEXANE (M) × $10^5$ |
|---|---|---|
| 5 | (+) 0.05 | 3.4 |
| 11 | (+) 0.07 | 3.8 |
| 30 | (+) 0.15 | 4.2 |
| 60 | (+) 0.26 | 5.1 |
| 120 | (+) 0.46 | 5.9 |
| 210 | (+) 0.70 | 6.8 |
| 300 | (+) 0.98 | 7.6 |
| 1350 | (+) 2.80 | 11.1 |

TABLE 5-continued

TREATED TUBE (initial weight of tube was 1.296 g.)

| EXTRACTION TIME IN HEXANE (MIN.) | % WEIGHT LOST (−) GAIN (+) | CONCENTRATION OF DOP IN THE HEXANE (M) × $10^5$ |
|---|---|---|
| 3105 | (+) 5.78 | 18.8 |
| 4215 | (+) 7.09 | 22.2 |

If all the DOP will be extracted, the concentration of the DOP in the hexane will be $1232.74 \times 10^{-5}$. Thus, the amount of DOP after 4215 min. of extraction is 1.8%. The tube (1.5033 g) after extraction in n-hexane was immersed in tetrahydrofuran. As expected, part of the PVC tube was not any more soluble in tetrahydrofuran. The soluble part was the rest of the PVC tube and the DOP. The unsoluble PVC weighed 0.12 g which included 18.3% S and 19.6% Cl. The soluble PVC weighed 0.75 g which included 3.97% S and 50.5% Cl. The amount of DOP recovered (checked by optical spectrum) was 0.40 g.

TABLE 6

UNTREATED TUBE (initial weight of tube was 1.552 g.)

| EXTRACTION TIME IN HEXANE (MIN.) | % WEIGHT LOST (−) GAIN (+) | CONCENTRATION OF DOP IN THE HEXANE (M) × $10^5$ |
|---|---|---|
| 5 | (−) 1.12 | 85.4 |
| 30 | (+) 0.06 | 85.4 |
| 60 | (+) 3.03 | 85.4 |
| 270 | (+) 4.96 | 200.8 |
| 1320 | (−) 5.61 | 576.1 |
| 2760 | (−) 10.20 | 658.1 |

If all the DOP will be extracted the concentration of the DOP in the hexane will be $1372.95 \times 10^{-5}$M. thus, the % weight of DOP extracted by hexane after 2760 min. is 47.9.

EXAMPLE 5

Replacement of Chlorine Ions bY Nitrate Ions

PVC tubes plasticized with dioctylphthalate (DOP) were immersed in Mixture No. 2 (100 ml water, 5 g sodium diethyldithiocarbamate and 1.5 g tetrabutylammonium hydrogensulfate) at 89° C. for 75 min and then washed with water. One of the tubes was further immersed in a hot water bath (77° C.) containing 3.9M of NaNO$_3$ for 19 hr.

The extraction of DOP was carried out by immersion of the tubes in a glass bath containing 100 ml n-hexane. During the extraction, samples of n-hexane were withdrawn and analyzed for their DOP content by spectrophotometric technique. The results of extraction by n-hexane of treated plasticized PVC tubes with no post treatment in salt solution, with post treatment in NaNO$_3$ solution and of untreated plasticized PVC tubes are shown in Tables 7, 8 and 9, respectively, and in FIG. 1.

TABLE 7

Extraction by n-hexane of plasticized PVC tubes after treatment in Mixture 2

| O.D. at 275 n.m. L = 1 cm. | Weight Change % | Sample Weight Gr. | Extraction Time (Min.) |
|---|---|---|---|
| 0.09 | 0.62 | 1.5263 | 30 |
| 0.12 | 2.09 | 1.5486 | 330 |
| 0.21 | 5.40 | 1.5987 | 1365 |
| 0.50 | 6.14 | 1.6100 | 1755 |

TABLE 7-continued

Extraction by n-hexane of plasticized PVC tubes after treatment in Mixture 2

| O.D. at 275 n.m. L = 1 cm. | Weight Change % | Sample Weight Gr. | Extraction Time (Min.) |
|---|---|---|---|
| 0.60 | 7.83 | 1.6355 | 2790 |
| 0.66 | 11.14 | 1.6857 | 5670 |
| 0.83 | 12.49 | 1.7062 | 7110 |
| 1.00 | 12.48 | 1.7060 | 8445 |

TABLE 8

Extraction by n-hexane of plasticized PVC tubes after treatment in Mixture 2, washing with water and immersion in NaNO$_3$ solution (3.9 M) for 19 hr at 77° C.

| O.D. at 275 n.m. L = 1 cm. | Weight Change % | Sample Weight g | Extraction Time (Min.) |
|---|---|---|---|
| 0.095 | 0.145 | 1.5190 | 30 |
| 0.100 | 0.342 | 1.5220 | 330 |
| 0.105 | 0.784 | 1.5287 | 1350 |
| 0.110 | 0.999 | 1.5318 | 1755 |
| 0.115 | 1.351 | 1.5373 | 2790 |
| 0.130 | 2.650 | 1.5570 | 7110 |
| 0.160 | 3.342 | 1.5675 | 8445 |

TABLE 9

Extraction by n-hexane of plasticized PVC tubes without any treatment

| O.D. at 275 n.m. L = 1 cm. | Weight Change % | Sample Weight g | Extraction Time (Min.) |
|---|---|---|---|
| 1.5 | −1.16 | 1.534 | 15 |
| 1.5 | −0.71 | 1.541 | 30 |
| 1.5 | 0.06 | 1.553 | 60 |
| — | 3.02 | 1.599 | 180 |
| 3.5 | 4.96 | 1.629 | 270 |
| 10.1 | −5.60 | 1.465 | 1320 |
| 11.6 | −10.24 | 1.393 | 2760 |

EXAMPLE 6

Controlled slow release of organic compound from PVC tubes.

Tubes made of plasticized PVC with dioctylphatalate (33% weight) were immersed in a water solution (300 ml) containing 15 g sodium diethyldithiocarbamate and 4.5 gr terbutyl-ammonium hydrogensulfate, at 89° C. for 75 min and then washed in water. After drying, the tubes were treated with either hot water at 77° C. or 2 M solution of NaNO$_3$ at 77° C. for 19 hr, dried and then extracted with 200 cc of n-hexane. The rate of release of encapsulated dioctylphatalate was measured. The results are summarized in Table 10.

TABLE 10

Rate of release of occluded DOP from PVC tubes

| Release of DOP | Untreated PVC tube | Treated PVC No post treatment | Treated PVC Post treated with NaNO$_3$ |
|---|---|---|---|
| Rate g/cm$^2$/day | $2.2 \times 10^{-1}$ | $9.36 \times 10^{-3}$ | $2.14 \times 10^{-4}$ |

EXAMPLE 7

A film of plasticized PVC was prepared by casting a cyclohexanone solution of a mixture of a copolymer of vinyl chloride and vinyl acetate (25%) with dioctylphtalate (DOP) in a weight ratio of 60:40 on a glass plate, to form a dry film of 0.5 mm final thickness. This film was immersed at 86° C. for 50 min in a water solution (300 ml) containing sodium diethyldithiocarbamate (15 g) and tetrabutylammonium chloride (4.5 g). After the reaction, the plasticized film was removed, washed with water and dried in vacuum for 12 hr at room temperature. Extraction of the treated films and similar non-treated films was carried out in hexane at room temperature. Samples of hexane were withdrawn from the extraction vessel and were analyzed for their DOP content. The results are shown in Table 11.

TABLE 11

| Unreacted plasticized copolymer film | | Treated plasticized copolymer film | |
|---|---|---|---|
| Time (min.) | % DOP extracted | Time (min) | % DOP extracted |
| 5 | 6.53 | 5 | 0.82 |
| 20 | 16.93 | 20 | 1.78 |
| 60 | 36.94 | 60 | 3.11 |
| 90 | 49.59 | 90 | 4.30 |
| 120 | 56.73 | 120 | 5.93 |
| 245 | 66.93 | 220 | 7.08 |
| 330 | 73.46 | 330 | 7.71 |

EXAMPLE 8

In order to investigate the effect of reaction time on the % of extracted DOP, plasticized PVC tubes were immersed at 85° C. in a water solution (300 ml) containing sodium diethyldithiocarbamate (15 g) and tetrabutylammonium chloride (4.5 g), for different periods of time.

The tubes were removed from the reaction mixture at different times and dried for 12 hr under vacuum at room temperature. The tubes were immersed in 150 ml of hexane. Samples of hexane were withdrawn from the extraction vessel and were analyzed by spectrophotometer for their DOP content. The results are shown in Table 12.

TABLE 12

| Extraction Time (min) | % DOP extracted 10 min reaction | % DOP extracted 20 min reaction | % DOP extracted 30 min reaction |
|---|---|---|---|
| 10 | 1.18 | 0.53 | 0.43 |
| 35 | 2.67 | 0.96 | 0.91 |
| 70 | 4.28 | 1.28 | 1.23 |
| 130 | 6.64 | 1.76 | 1.60 |
| 225 | 11.34 | 2.51 | 2.19 |
| 335 | 23.30 | 3.05 | 2.73 |
| 503 | 41.00 | 4.07 | 2.94 |
| 1330 | 65.10 | 26.23 | 5.46 |
| 1700 | 68.30 | 35.90 | 6.42 |
| 2835 | 75.27 | 48.50 | 8.04 |
| 3168 | 75.48 | 50.32 | 8.77 |

These results show that the rate of release of substances occluded within the PVC matrix, such as pesticides, fertilizers, drugs and the like, can be controlled by suitable combination of the conditions of the treatment and of the post treatment according to the process of the invention.

It will be obvious to those skilled in the art that various changes may be made in the invention without departing from its scope and the invention is not to be considered limited to what is described in the specification.

I claim:

1. A crosslinked PVC product characterized by a gradient crosslinking density, with a high crosslinking density on the outer surface and/or near the surface and a low or none crosslinking density at the bulk of the product.

2. A crosslinked PVC product according to claim 1 wherein the PVC is crosslinked with a dithiocarbamate compound.

3. A process for the preparation of a PVC product having a crosslinked outer surface characterized by a gradient crosslinking density, with a high crosslinking density on said outer surface and a lower or no crosslinking density within the bulk of the product, the process comprising immersing an un-crosslinked PVC product in a water solution of a water-soluble crosslinking material and a phase transfer catalyst, at a temperature of at least about 60° C., said crosslinking material being capable of reacting with chlorine containing polymers by displacing the chlorine and then further reacting with a second chlorine to form a crosslinking network, said crosslinking material being present in an amount sufficient to be capable of diffusing into the PVC product so as to displace at least one chlorine atom along polymeric chains of said PVC to provide substituted polymer molecules, and maintaining said PVC product within said water solution at said temperature for a time sufficient to effect diffusion of said crosslinking material and said phase transfer catalyst into the PVC product so as to effect displacement of at least one chlorine atom along polymeric chains of said PVC to provide substituted polymer molecules, and triggering a chemical crosslinking of said substituted polymer molecules to produce a crosslinked outer surface characterized by a gradient crosslinking density with a high crosslinking density on said outer surface and a low or no crosslinking density within the bulk of the PVC product.

4. A process according to claim 3 wherein the crosslinking material is a dithiocarbamate compound of the formula

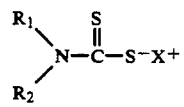

wherein $R_1$ is alkyl, optionally substituted by hydroxy or acyloxy, or $R_1$ is aralkyl; $r_2$ is hydrogen or $R_1$, or $R_1$ and $R_2$ together with the N atom form a ring optionally containing an N, S or O atom and/or a carbonyl group and optionally condensed to a benzene ring, and $X^+$ is a cation.

5. A process according of claim 4 wherein the crosslinking material is sodium diethyldithiocarbamate.

6. A process according to claim 3 wherein the crosslinking material is a bifunctional or trifunctional thiol compound of the formula HS-R-SH or R-(SH)$_3$, in which R is alkyl, aryl, aralkyl, heterocyclyl or a residue derived from polyethylene oxide or polypropylene oxide.

7. A process according to claim 3 wherein the phase transfer catalyst is a quaternary ammonium salt, a tertiary alkyl phosphonium salt, a $C_6$–$C_{15}$ polyethylene oxide or a cyclic crown ether.

8. A process according to claim 3 wherein the crosslinking material is sodium diethyldithiocarbamate and the phase transfer catalyst is tetrabutylammonium chloride.

9. A process according to claim 3 wherein the water solution further contains an organic or inorganic salt.

10. A process according to claim 3 wherein the crosslinked PVC product is further treated with a water solution of an inorganic or organic salt.

11. A process according to claim 3 wherein the crosslinking material is sodium diethyldithiocarbamate and the phase transfer catalyst is tetrabutylammonium chloride.

12. A process according to claim 3 wherein the crosslinked plasticized PVC product is further reacted with a water solution containing an inorganic or an organic salt.

13. A process according to claim 12 wherein the salt has a cation selected from the group of an alkali, earth alkali and a transition metal residue and an anion selected from the group of $NO_3^-$, $SO_4^{-2}$, $PO_4^{-3}$ and $CF_3COO^-$.

14. A process according to claim 3, wherein said PVC product is placitized, said process serving to protect the plasticized PVC product from the migration of plasticizer therefrom.

15. A process according to claim 3, wherein said uncrosslinked PVC product constitutes a PVC matrix having occluded therewithin a biochemically active compound capable of being slowly released from said PVC product.

16. A process according to claim 15, wherein said biochemically active substance is selected form the group consisting of a pesticide, a fertilizer and a drug.

17. A process according to claim 3, wherein said PVC polymer is selected from the group consisting of PVC homopolymer and PVC copolymers with polyvinyl acetate, polyvinyl alcohol or polyacrylonitrile.

18. A process according to claim 3, wherein the concentration of the phase transfer catalyst in said water solution is in the rang of 0.1-0.5% said cross-linking material is in the range of 2-10%, and said temperature is 60°-90° C.

19. A PVC product made by the process of claim 3.

20. A PVC product made by the process of claim 14.

21. A PVC product made by the process of claim 15.

22. A process according to claim 16 wherein the crosslinked PVC product containing the occluded substance is further reacted with a water solution containing an inorganic or organic salt.

23. A process according to claim 22 wherein the salt has a cation selected from the group of an alkali, earth alkali and a transition metal residue and an anion selected from the group of $NO_3^-$, $SO_4^{-2}$, $PO_4^{-3}$ and $CF_3COO^-$.

24. A process for the preparation of a PVC product having a crosslinked outer surface characterized by a gradient crosslinking density, with a high crosslinking density on said outer surface and a low or no crosslinking density within the bulk of the product, the process comprising
  immersing an un-crosslinked PVC product in a water solution at said temperature of a water-soluble crosslinking material and a phase transfer catalyst, at a temperature of at least about 60° C., said crosslinking material being capable of reacting with chlorine containing polymers by displacing the chlorine and then further reacting with a second chlorine to form a crosslinking network.
  maintaining said PVC product within said water solution for a time sufficient to effect diffusion of said crosslinking material and said phase transfer catalyst into the PVC product so as to effect displacement of at least one chlorine atom along polymeric chains of said PVC to provide substituted polymer molecules, and triggering a chemical crosslinking of said substituted polymer molecules,
  wherein the crosslinked PVC product is further treated with a water solution of an inorganic or organic salt having a cation selected form the group consisting of an alkali, earth alkali and a tradition metal residue and an anion selected from the group consisting of $NO_3-$, $SO_4^{-2}$, $PO_4^{-3}$ and $CF_3COO$.

* * * * *